United States Patent [19]

Koller et al.

[11] Patent Number: 4,918,007
[45] Date of Patent: Apr. 17, 1990

[54] PROMOTER ARRANGEMENT FOR STREPTOMYCETES VECTORS

[75] Inventors: Klaus-Peter Koller, Bad Soden am Taunus; Günther J. Riess, Frankfurt am Main, both of Fed. Rep. of Germany

[73] Assignee: Hoechst Aktiengesellschaft, Frankfurt am Main, Fed. Rep. of Germany

[21] Appl. No.: 917,066

[22] Filed: Oct. 8, 1986

[30] Foreign Application Priority Data

Oct. 10, 1985 [DE] Fed. Rep. of Germany ....... 3536182

[51] Int. Cl.$^4$ ...................... C12P 21/00; C12P 21/02; C12N 15/00; C12N 1/20; C07H 15/12
[52] U.S. Cl. .................. 435/69.2; 435/69.1; 435/172.3; 435/252.35; 435/320; 435/886; 435/70; 935/6; 935/27; 935/41; 935/61; 935/75; 536/27
[58] Field of Search ............ 435/68, 70, 91, 169, 435/172.1, 172.3, 886, 320, 252.35; 536/27; 935/6, 8, 9, 10, 11, 22, 23, 24, 27, 29, 38, 39, 41, 59, 60, 61, 72, 75

[56] References Cited

U.S. PATENT DOCUMENTS

4,226,764 10/1980 Oeding et al. .................. 260/112
4,451,455 5/1984 Vertesy et al. .................. 424/177

FOREIGN PATENT DOCUMENTS

0105521 4/1984 European Pat. Off. .
0152830 8/1985 European Pat. Off. .
0187630 7/1986 European Pat. Off. .
3331860 3/1985 Fed. Rep. of Germany .

OTHER PUBLICATIONS

Old et al., Principles of Gene Manipulation (Studies in Microbiology, vol. 2) (1985) p. 182.
Hopwood et al., Genetic Manipulation of Streptomyces, a Laboratory Manual, the John Innes Foundation, Norwich England, (1985), pp. 292 and 293.
Chemical Abstracts, vol. 103, Abstract #66066c, issued Sep. 1985, Koller, Klaus Peter, 1985, Tendamislat Production, Ger. Offen. DE 3,331,860.
Katz et al., 1983, *J. Gen. Microbiology* 129:2703-2714.
Biological Abstracts, vol. 65, Abstract #70404, Backman et al. 1978, Maximizing Gene Expression on a Plasmid Using Recombination in vitro, Cell 13(1): 65-72.
Adams et al., 1984, *J. Biol. Chem.* 259(12): 7399-7403.
Chemical Abstracts vol. 103: Abstract #99720q, issued Sep. 1985, Murooka et al., 1985, Efficient Expression of a Promoter Controlled Gene: Tandem Promoters of Lambda $P_R$ and $P_L$ Functional in Enteric Bacteria, J. Biotechnol. 2(5): 303-316 (Eng.).
Jaurin et al., Gene 28: 83-91 (1984).
European Search Report: EP 86 11 3627.

*Primary Examiner*—T. G. Wisemann
*Assistant Examiner*—Richard C. Peet
*Attorney, Agent, or Firm*—Finnegan, Henderson, Farabow, Garrett and Dunner

[57] ABSTRACT

A tandem arrangement of two promoters which are each active in Streptomyces is provided. The tandem arrangement provides a considerable increase in protein expression.

14 Claims, 1 Drawing Sheet

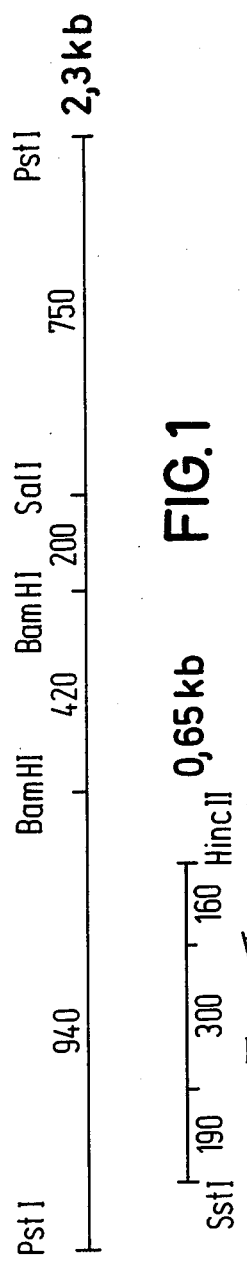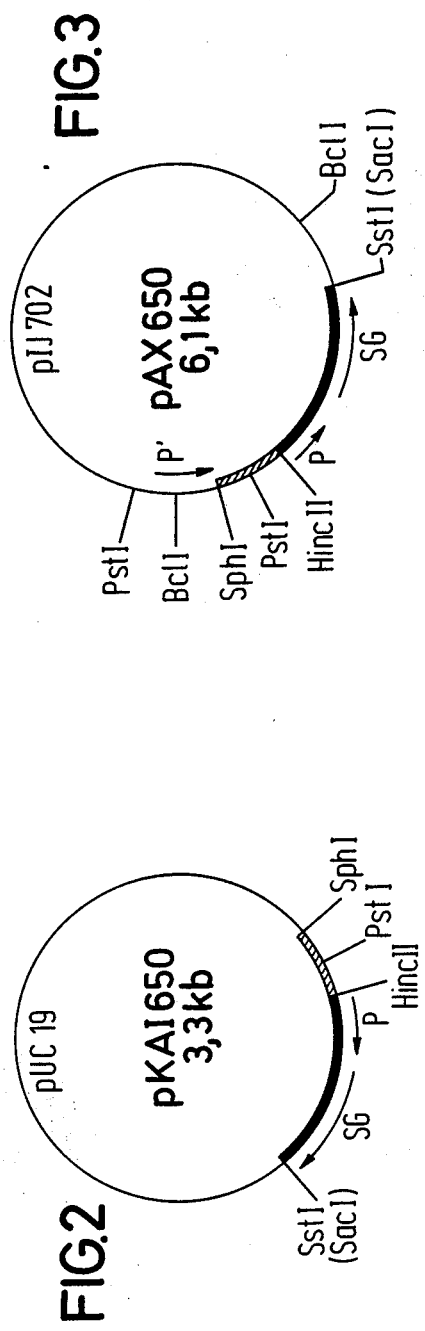

PROMOTER ARRANGEMENT FOR STREPTOMYCETES VECTORS

The invention relates to a combination of promoters which are effective in Streptomycetes and are arranged in sequence and in the correct reading frame. This "tandem arrangement" brings about a considerable increase in protein expression. The invention also relates to vectors which contain this promoter arrangement, to Streptomycetes host strains which contain such vectors, and to their use for the preparation of protein. Preferred embodiments of the invention are illustrated in detail below and defined in the patent claims.

Relatively little is yet known about the DNA structure of promoters which are effective in Streptomycetes. It has now been found that by arranging two Streptomycetes promoters in the correct reading frame it is possible to increase protein expression to an unexpected extent. It is not necessary for this that the two promoters are arranged directly in sequence, which would moreover be associated with difficulties given the fact that the present state of knowledge of the DNA structure of these promoters is still low. Thus, it suffices for the promoters to be arranged in the correct reading frame with respect to one another and to the structural gene which is to be expressed, it being possible for a DNA segment of variable length to be located between the two promoters. The most favorable dimension of this DNA bridge can readily be determined by simple preliminary experiments, it being possible to use, for example, chemically synthesized DNA bridges in the form of suitable linkers or adaptors.

A suitable promoter which is effective in Streptomycetes can be obtained from the hybrid plasmid pKAI 1 which is described in German Offenlegungsschrift 3,331,860. For this purpose, the 2.3 kb DNA segment which is illustrated in detail in FIG. 2 in this Offenlegungsschrift is reacted with the restriction enzymes Sst I and Hinc II, and the fragment comprising 650 bp is isolated. This DNA fragment contains the structural gene for the α-amylase inhibitor "tendamistat" and the relevant promoter. This DNA sequence is located within the segment comprising 940 bp between the restriction sites for the enzymes Pst I and Bam HI (FIG. 2 of German Offenlegungsschrift 3,331,860).

Another promoter which is suitable for the "tandem arrangement" according to the invention is to be found in the commercially available plasmid pIJ 702 (E. Katz et al., J. Gen. Microbiol. 129 (1983) 2703-2714; D. A. Hopwood et al., Genetic Manipulations of Streptomyces, A Laboratory Manual, The John Innes Foundation, Norwich, England, 1985, page 292). For this purpose, this plasmid is cut with the restriction enzymes Sph I and Pst I, and the fragment comprising 350 bp is isolated. It is also possible to react the plasmid with the restriction enzymes Sph I and Bcl I, and to isolate the DNA fragment comprising 270 bp. The promoter for the mel gene which codes for the protein tyrosinase is located on this 270 bp DNA fragment.

These DNA fragments with the mel promoter can then be integrated—in the correct reading frame—into any desired expression vector in such a manner that they are located upstream of another promoter which is effective in Streptomycetes or are located between this promoter and the structural gene.

In another embodiment of the invention the mel promoter is not isolated from the plasmid pIJ 702, but the structural gene and the second promoter are integrated—again in the correct reading frame—into this plasmid.

It is convenient to incorporate the second promoter and the structural gene as a unit downstream of the mel promoter, that is to say, for example, to make use of the said DNA fragment having the tendamistat structural gene and the relevant promoter. This gene structure results in correct expression, which is increased by approximately the factor of 10, and secretion of the α-amylase inhibitor tendamistat.

With plasmids of high copy number per cell the expression of proteins may diminish over long periods of fermentation. In such cases vectors of low copy number are recommended.

It is also possible, in accordance with this gene structure which is given here only by way of example, to insert in such "tandem arrangements" other promoters which are effective in Streptomycetes and to express any desired structural genes.

The invention is illustrated in detail in the examples which follow.

EXAMPLE 1

A 650 bp Hinc II-Sst I fragment is isolated from 7 μg of DNA from the plasmid pKAI 1 (German Offenlegungsschrift 3,331,860) by electroelution. The arrangement of this fragment within the 2.3 kb fragment from the plasmid pKAI 1 is represented in FIG. 1, in which "SG" indicates the structural gene for the α-amylase inhibitor. In addition to the structural gene, the 650 bp fragment contains all the regulatory regions necessary for expression in *Streptomyces lividans* TK 24.

The commercially available *E. coli* vector pUC 19 (C. Yanisch-Perron et al., Gene 33 (1985), 103-119; New England Biolabs 1985/86 Catalog, pages 90/91; BRL, Bethesda Research Laboratories Catalogue & Reference Guide, pages 136/137) is double-digested with the restriction endonucleases Hinc II and Sst I, and the linearized plasmid is ligated with the above-mentioned 650 bp Sst I-Hinc II fragment having the tendamistat gene. After transformation of *E. coli* JM 101, clones containing the recombinant plasmid, which is called pKAI 650 and which contains the incorporated 650 bp fragment, are isolated. This plasmid is shown in FIG. 2 (not to scale), in which P indicates the promoter region.

Isolated pKAI 650 plasmid DNA is subjected to double-digestion with the restriction endonucleases Sst I and Sph I or with Sst I and Pst I and then to preparative gel electrophoresis and electroelution, and the fragment comprising approximately 650 bp is isolated.

EXAMPLE 2

The plasmid pIJ 702 (obtainable from the John Innes Foundation, Norwich, England) is digested with the restriction endonucleases Sst I and Sph I, and the 400 bp Sst I-Sph I fragment is separated from the remaining vector DNA by agarose gel electrophoresis. 1 μg of the isolated, purified vector DNA is ligated with 0.3 μg of the 650 bp Sst I-Sph I fragment from pKAI 650 (Example 1), and *Streptomyces lividans* TK 24 (obtainable from the John Innes Foundation) is transformed with the ligation product in a manner known per se. The desired clones are selected by resistance to thiostreptone and production of the α-amylase inhibitor, using the following plate test:

5 ml of an aqueous solution containing 0.4 to 1.0 mg/ml pancreatin are poured onto the colonies, and the mixture is incubated at 37° C. for one hour. The solution is then removed and replaced by 5 ml of a 2% by weight starch agar. After incubation at 37° C. for two hours, for the development 5 ml of an iodine/potassium iodide solution are poured over the plates. Colonies with a blue halo indicate that the clones synthesize and excrete tendamistat.

The recombinant plasmid which is called pAX 650 and which brings about the synthesis of the α-amylase inhibitor tendamistat is represented in FIG. 3 (not to scale). In this figure, P' denotes the promoter region of the mel gene from pIJ 702.

EXAMPLE 3

(COMPARISON EXAMPLE)

The process is carried out as in Example 2, but the Pst I-Sst I fragment comprising 650 bp is eliminated from the plasmid pIJ 702, and the remaining plasmid is ligated with the Sst I-Pst I fragment comprising about 650 bp from pKAI 650. The recombinant plasmid pAX 651 which is thus obtained shows in the test for α-amylase inhibition a figure which is about one-tenth that with the plasmid pAX 650 (Example 2).

EXAMPLE 4

The "shuttle vector" pSW1 (European Patent Application with the publication number 0,158,201, FIG. 26) is digested partially with the restriction enzyme Bcl I and linear fragments of 16.6 kb length are isolated after electrophoresis in a 0.4% agarose gel. The isolated DNA fragments are extracted with buffered phenol solution and precipitated with ethanol.

The DNA fragments purified in this manner are ligated with the 1.81 kb Bcl I fragment from pAX650 which contains the complete gene for the α-amylase inhibitor. The ligation mixture is transformed into *S. lividans* TK 24. Recombinant clones which are resistant to thiostrepton produce and excrete the α-amylase inhibitor tendamistat in constant yield even over long periods of fermentation time.

We claim:

1. A tandem arrangement of two promoters, each being active in Streptomyces, at least one of said promoters being selected from the group consisting of a promoter located in the 350 bp Pst I-Sph I fragment of plasmid pIJ 702 and a promoter located in the 650 bp Hinc II-Sst I fragment of plasmid pKAI 1, which fragment is located within the 0.94 kb Pst I-Bam HI fragment.

2. An arrangement of promoters as claimed in claim 1, wherein one of the promoters is that located in the 350 bp Pst I-Sph I fragment of plasmid pIJ 702.

3. The arrangement of promoters as claimed in claim 2, wherein the promoter is located in the 270 bp Bcl I-Sph I fragment of plasmid pIJ 702.

4. An arrangement of promoters as claimed in claim 1, wherein one of the promoters is that located in the 650 bp Hinc II-Sst I fragment of plasmid pKAI 1 which fragment is located within the 0.94 kb Pst I-Bam HI fragment.

5. The arrangement of promoters as claimed in claim 4, wherein the second promoter is that located in the 350 bp Pst I-Sph I fragment of plasmid pIJ 702.

6. The arrangement of promoters as claimed in claim 4, wherein the second promoter is that located in the 270 bp Bcl I-Sph I fragment of plasmid pIJ 702.

7. A vector which is active in Streptomyces containing a promoter arrangement as claimed in claim 1.

8. A host cell of the genus Streptomyces containing a vector as claimed in claim 7.

9. A host cell as claimed in claim 8 which is of the species *S. lividans*.

10. A process for preparing a protein, which comprises causing expression of a gene operatively linked to a promoter arrangement of a vector as defined in claim 7 within a Streptomyces host cell.

11. A process as claimed in claim 10, wherein the host cell is *S. lividans*.

12. A process as claimed in claim 10, wherein the protein is tendamistat.

13. Plasmid pKAI 650 as shown in FIG. 2.

14. Plasmid pAX 650 as shown in FIG. 3.

* * * * *